United States Patent [19]
Barraquer et al.

[11] Patent Number: 6,110,202
[45] Date of Patent: Aug. 29, 2000

[54] INTRAOCULAR IMPLANT FOR CORRECTING SHORT-SIGHTEDNESS

[75] Inventors: Joaquin Barraquer, Barcelone, Spain; Gilles Bos, Sillingy, France

[73] Assignee: Corneal Laboratoires, Paris, France

[21] Appl. No.: 09/125,371

[22] PCT Filed: Feb. 19, 1997

[86] PCT No.: PCT/FR97/00306

§ 371 Date: Aug. 14, 1998

§ 102(e) Date: Aug. 14, 1998

[87] PCT Pub. No.: WO97/30657

PCT Pub. Date: Aug. 28, 1997

[30] Foreign Application Priority Data

Feb. 20, 1996 [FR] France .................................. 96 02053

[51] Int. Cl.⁷ ....................................................... A61F 2/16
[52] U.S. Cl. ........................ 623/6.43; 623/6.43; 623/6.11; 623/6.14; 623/6.38; 623/6.4
[58] Field of Search .................................. 623/4, 5, 6, 4.1, 623/6.11, 6.14, 6.38, 6.39, 6.4, 6.42, 6.43

[56] References Cited

U.S. PATENT DOCUMENTS

| | | | |
|---|---|---|---|
| 4,277,851 | 7/1981 | Choyce | 623/6 |
| 4,585,456 | 4/1986 | Blackmore . | |
| 4,664,666 | 5/1987 | Barrett | 623/6 |
| 4,769,035 | 9/1988 | Kelman . | |
| 5,071,432 | 12/1991 | Baikoff | 623/6 |
| 5,300,117 | 4/1994 | Baikoff . | |
| 5,609,630 | 3/1997 | Crozafon | 623/6 |
| 5,928,282 | 7/1999 | Nigam | 623/6 |

FOREIGN PATENT DOCUMENTS

| | | |
|---|---|---|
| 0 477 109 A1 | 3/1992 | European Pat. Off. . |
| 0 492 126 A2 | 7/1992 | European Pat. Off. . |
| 4211265 | 7/1993 | Germany . |
| WO 91 13597 | 9/1991 | WIPO . |
| WO 95 28897 | 11/1995 | WIPO . |

*Primary Examiner*—Dinh X. Nguyen
*Attorney, Agent, or Firm*—Wolf, Greenfield & Sacks, P.C.

[57] ABSTRACT

A posterior-chamber intraocular implant for correcting short-sightedness in a phakic eye. Comprises a substantially circular optical portion (30) consisting of a front dioptric surface (40) and a rear dioptric surface (42) and a haptic portion. The haptic portion includes two extensions (32, 34) joined to the edge of the optical portion, of which the ends are spaced apart by a distance greater than the diameter of a dilated pupil, and two portions (52, 54) for attachment, the front surface of each extension comprising a toroidal portion (44) joined to the front dioptric surface, the rear surface of each extension comprising a toroidal portion (46) forming portion engaging the lens circumference and connected to the rear dioptric surface and a connecting portion (48), the rear dioptric surface and the toroidal portions of the rear surfaces of said extensions defining a recess (50) for freely altering the curvature of the front lens surface.

19 Claims, 2 Drawing Sheets

INTRAOCULAR IMPLANT FOR CORRECTING SHORT-SIGHTEDNESS

The present invention has for its object an intraocular implant for correcting short-sightedness.

More precisely, the invention has for its object an intraocular implant for correcting short-sightedness which is intended to be positioned in the posterior chamber of a phakic eye, i.e. an eye of which the lens was not removed during an operation for ablation of the cataract.

Two important types of intraocular implant intended for correcting short-sightedness can be cited. In the first type of implant, the latter is intended to be positioned in the anterior chamber of the eye. In accompanying FIG. 1, a human eye has been shown in horizontal section, comprising therefore the cornea 10, the iris 12 with the pupil 14 and the lens 16 contained in the capsular sac 18 itself joined by zonulas 21 on the inner wall of the eye.

Conventionally, anterior chamber 20 designates the space inside the eye which extends between the cornea 10 and the iris 12. On the other hand, posterior chamber designates all the internal part of the eye to the rear of the iris 14. This posterior chamber therefore comprises a zone 22 which extends between the iris 12 and the anterior face of the lens 16 and a zone 24 inset with respect to the lens 16.

In the first type of implant for short-sightedness, the latter is positioned in the anterior chamber 20. In this case, one of the difficulties encountered is that, in order to be able to correct the short-sightedness effectively, the optical portion of the implant necessarily presents a relatively thick edge. Taking into account the reduced dimensions of the anterior chamber, there is therefore a real risk of the edge of the optical portion of the implant, positioned in the anterior chamber, traumatizing the inner face of the cornea 10. Such traumatism may have serious consequences since the cells of the inner face of the traumatized cornea cannot regenerate and this affliction tends to develop towards the central portion of the cornea, i.e. the one which performs the most important role in vision.

This is why, in the second type of implant for short-sightedness, an implantation of the latter in the posterior chamber is proposed and, in the case of the phakic eye, in zone 22 of the posterior chamber, i.e. the one which extends between the iris and the anterior face of the lens 16.

The present invention concerns the second type of implant, i.e. a posterior chamber implant for phakic eye.

The positioning of such an implant also raises certain difficulties. In fact, the space between the posterior face of the iris and the anterior face of the lens 16 is relatively reduced. This results in the implant being in contact both with the posterior face of the iris and the anterior face of the lens. This problem is rendered still more complex as the pupil 14 dilates and contracts depending on the light conditions to which the eye is subjected and, on the other hand, depending on the desired or necessary accommodation, the shape of the lens 16 and in particular its anterior face 16a and therefore in particular the curvature of the front face 16a of the lens, is altered.

Furthermore, after having been positioned in the zone 22 of the posterior chamber, the implant is subjected to effects of pressure resulting from the aqueous humor and the vitreous humor present in the anterior chamber and the posterior chamber and external pressures which may be applied to the whole of the eye. It is necessary that, under the effect of these different pressures, there is no risk of the implant leaving the posterior chamber and passing into the anterior chamber.

It is an object of the present invention to provide an intraocular implant for short-sightedness for the posterior chamber of a phakic eye which better solves the problems set forth hereinabove, particularly by better allowing the respective deformations of the lens and the iris, while ensuring a very good holding of the implant in place in the posterior chamber.

To attain this object, the posterior-chamber intraocular implant for correcting short-sightedness in a phakic eye, comprising a substantially circular optical portion consisting of a front dioptric surface and a rear dioptric surface and a haptic portion, is characterized in that said haptic portion includes at least two extensions joined to the edge of the optical portion, of which the ends are spaced apart by a diametral distance greater than the diameter of a dilated pupil, and at least two portions for attachment on the wall of the chamber, the front surface of each extension comprising a toroidal portion joined to the front dioptric surface, said toroidal portions being adapted to allow slide of the posterior face of the iris on said implant, the rear surface of each extension comprising a toroidal portion joined to the rear dioptric surface and forming portion engaging the lens circumference, and a connecting portion, the rear dioptric surface and the toroidal portions of the rear surfaces of said extensions defining a recess with respect to the surface (S) containing said connecting portions for freely altering the curvature of the front lens surface.

It will be understood that, thanks to the presence of the extensions, the intraocular implant is well held in the posterior chamber, whatever the degree of dilation of the pupil of the iris. It will also be understood that, thanks to the presence of the recess formed in the posterior face of the optical portion of the implant, a free alteration of the curvature of the anterior face of the lens is allowed. It is also seen that, thanks to the presence of the toroidal engagement portions, the implant is in contact with the anterior face of the lens only by a peripheral zone not directly concerned by the vision and over a very reduced annular zone. Finally, it will also be understood that, thanks to the presence of the toroidal portion joined to the front dioptric surface of the implant, the iris may slide freely with respect to the anterior face of the implant during dilation or contraction of the pupil without there being a risk of the iris "sticking" on the implant.

Other characteristics and advantages of the invention will better appear from reading the following description of a preferred embodiment of the invention given by way of non-limiting example. The description refers to the accompanying Figures, in which:

FIG. 1, already described, shows the different parts of the inside of the human eye.

Figure 3:
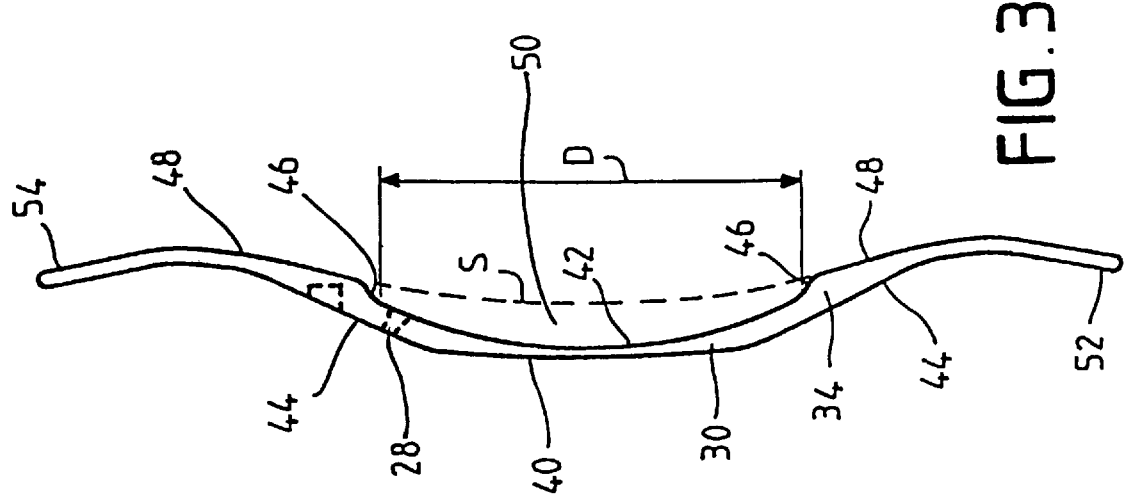
FIG. 3 is a side view of the implant of FIG. 2.
Figure 2:
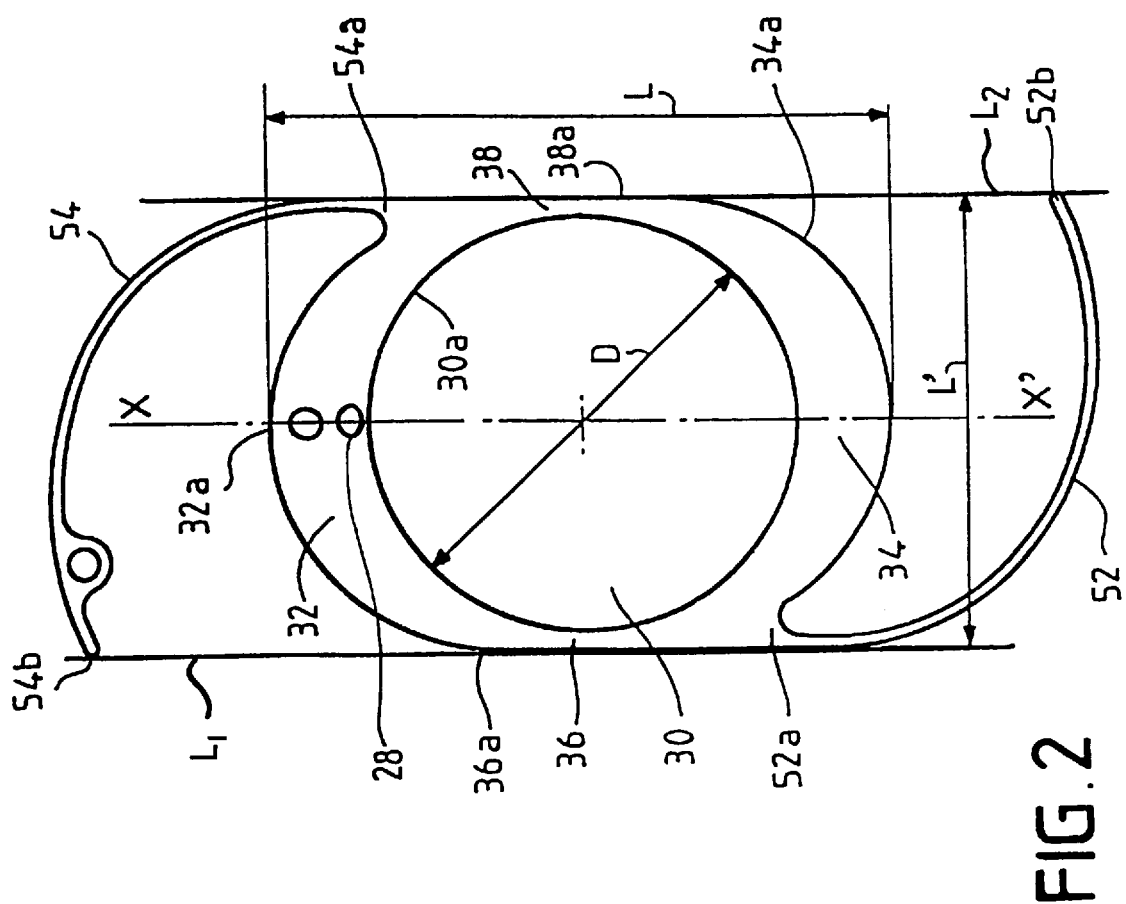
FIG. 2 is a view in front elevation of the implant for short-sightedness according to the invention.

Referring firstly to FIGS. 2 and 3, a preferred embodiment of the implant for short-sightedness will be described. This latter comprises a substantially circular optical portion 30 of diameter D. In the particular example described, this diameter is equal to 5.5 mm. More generally, the diameter D is included between 4 and 6 mm. At each end of the optical portion 30 in the direction of vertical axis XX', the implant comprises an extension referenced 32 and 34 respectively, which are joined to the periphery 30a of the optical portion. These extensions belong to the haptic portion of the implant. In the example considered, the extensions are limited by free edge 34a and 32a of substantially semi-circular form. In the example shown, the haptic portion also comprises two lateral portions 36 and 38 which join the extensions 32 and 34 on either side of the optical portion 30. The optical portion 30 is, of course, limited by a front dioptric surface 40 which, in the example in question, is planar, and by a rear dioptric surface 42 which is concave. The anterior face of the extensions 32 and 34 is limited by a toroidal surface portion 44 which is joined to the periphery of the front dioptric surface 40. If the posterior face of the extensions 32 and 34 is now considered, it is seen that it is defined firstly by a toroidal surface portion 46 forming engagement surface then by a zone of connection 48, which is also toroidal or truncated. It is also seen that, with respect to the surface S which contains the connection surfaces 48 of the extensions 32 and 34, the rear dioptric surface 42 and the toroidal zone 46 define a posterior recess 50 whose function will be set forth hereinafter. The lateral portions 36 and 38 present anterior and posterior faces which extend the anterior and posterior faces of the extensions 32 and 34.

As shown more clearly in FIG. 2, the distance between the ends of the extensions 32 and 34, referenced L in FIG. 2, is substantially greater than the diameter D of the optical portion. In the example in question, L is equal to 8 mm. More generally, L is included between 7 and 9 mm.

Finally, the haptic portion of the implant comprises, in addition to the extensions 32 and 34 and preferably the lateral zones 36 and 38, two attachment loops 52 and 54 which comprise an end 52a, 54a for connection on the extensions 32 or 34 and a free end 54b, 52b. In the particular example in question, the loops 52 and 54 are of the so-called "C" type.

As is well known, the free ends of the loops 52b and 54b are intended to engage on the inner wall of the posterior chamber in order to hold the implant in place so that the optical portion 30 remains correctly centered, particularly with respect to the pupil 14.

Figure 5:
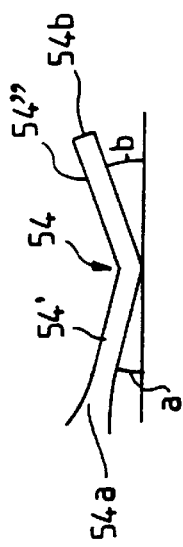
FIG. 5 is a view in detail of the implant showing a loop for attaching the haptic portion.
Figure 1:
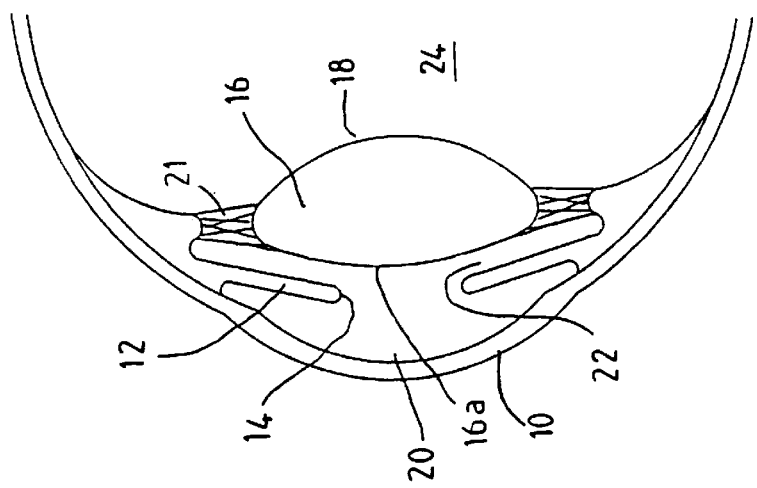

In order to avoid, under the action of the pressures or of an external stress, the optical portion of the implant moving in the direction of the optical axis of the eye, each loops 52 and 54 preferably presents an angulation in a plane containing the optical axis. In FIG. 5, loop 54 has been shown more particularly; it is seen that the first portion 54' of the loop closest to the end 54a makes an angle a with a plane orthogonal to the optical axis and that the second portion 54" closest to the end 54b makes an angle b with this same direction. The angulation corresponding to angle a tends to move the loop away from the anterior face of the optical portion while angulation b tends to bring it closer. This angulation means that, under the effect of stresses applied to the loops in the direction of the principal plane of the implant, any axial displacement of the implant is substantially avoided.

It goes without saying that the means for attachment of the haptic portion might take a form other than the loops shown in FIG. 2.

It should also be noted that, in order to avoid an effect of suction of the implant with respect to the lens, due to the connection surfaces 48 of the extensions and the lateral portions 36 and 38, there is provided, either in the extensions or in these portions of the lateral parts, a passage 28 communicating the recess 50 with the interior of the eye in order to render pressures equal. It is also possible to provide that the total width L' of the implant at the level of the lateral zones 36 and 38 be such that a natural passage is produced between the engagement zones of the lateral portions and the anterior face of the lens. In that case, the pressures are rendered equal automatically.

Likewise preferably, in order to facilitate introduction of the implant in the eye, the lateral dimensions of the loops 52 and 54 are less than or equal to L'.

More precisely, the lateral portions of the haptic portion each present a substantially rectilinear free edge which joins the substantially semi-circular edges of said extensions.

Figure 4:
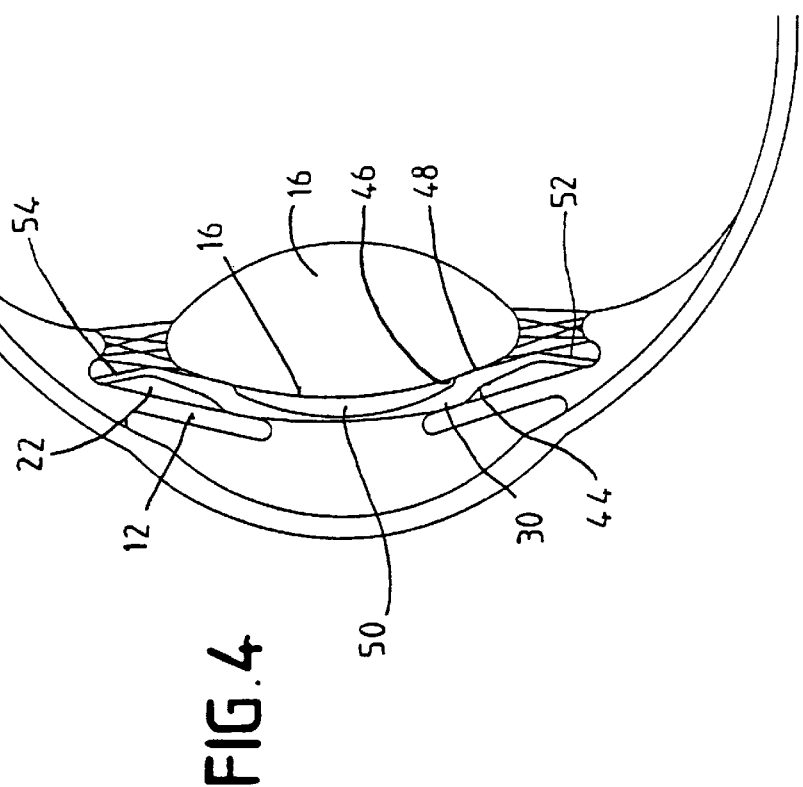
FIG. 4 is a top view showing the positioning of the implant for short-sightedness in the posterior chamber of the eye.

FIG. 4 shows the implant for short-sightedness positioned in the posterior chamber 22 of the eye, the lens being at rest, i.e. without there being accommodation. This Figure shows that the anterior face of the implant is in contact with the posterior face of the iris 12 via the toroidal surface 44, which allows the iris to slide on the anterior face of the implant during dilations or contractions of the pupil.

FIG. 4 also shows that the posterior face of the implant is in contact with the anterior face of the lens 16a via the toroidal engagement surface 46 which effectively performs its role of engagement as the radius of curvature of the anterior face of the lens decreases to effect accommodation, FIG. 4 showing the lens in its state of "non-accommodation". Moreover, the contact between the lens and the surface 46 is a contact between a sphere and a toroidal surface portion. The contact surface is therefore annular and very reduced. The first consequence of this is that this contact is produced on the peripheral zone of the lens and not on its central zone. The second consequence is that the central portion of the lens is opposite the recess 50 of the posterior face of the implant. This recess therefore allows an alteration of the radius of curvature of the anterior face 16a of the lens without there being any contact between the lens and the posterior face 42 of the optics of the implant. This therefore allows the curvature of the lens to be freely altered.

The projection of the loops on a plane orthogonal to the optical axis of the implant is preferably entirely contained in that portion of said plane limited by the straight lines $L_1$, $L_2$ of the plane containing the projections on this plane of the free edges of the lateral portions of the haptic portion.

What is claimed is:

1. A posterior-chamber intraocular implant for correcting short-sightedness in a phakic eye, having a natural lens, said implant comprising:

a substantially circular optical portion comprising a front dioptric surface and a rear dioptric surface and having a periphery and an optical axis;

at least two extensions having an inner edge connected to the periphery of the optical portion and an outer edge, a maximum distance between the outer edges of the extensions being greater than a diameter of a dilated pupil, each extension having a front surface and a rear surface, the front surface of each extension comprising a toroidal portion joined to the front dioptric surface for allowing a posterior face of an iris of an eye to slide on said implant, the rear surface of each extension comprising a toroidal portion connected to the rear dioptric surface, the toroidal portion of the rear surface being structured to engage a periphery of a lens of an eye, and a connecting portion for connecting the toroidal portion with the outer edge of the extension, the connecting portions of the at least two extensions being contained in a common surface, the rear dioptric surface and the toroidal portions of the rear surfaces of said extensions defining a recess with respect to the common surface for allowing a free altering of a curvature of a front surface of a natural lens of an eye; and at least two attachment portions distinct from the at least two extensions, each attachment portion having a first end connected to the outer edge of an associated extension and a second end being structured to be in contact with an inner wall of a posterior chamber of an eye.

2. The intraocular implant according to claim 1, wherein the at least two extensions are diametrically opposed with respect to the optical portion.

3. The intraocular implant according to claim 2, further comprising two lateral portions, each lateral portion having an inner edge connected to the periphery of the optical portion between the two extensions, a free edge, a front face extending from the toroidal portion of the front surface of the two extensions and a rear face extending from the toroidal portion of the rear surface of the two extensions.

4. The intraocular implant according to claim 3, further comprising at least one hole passing through the implant and opening into a front and a rear surface of the implant.

5. The intraocular implant according to claim 2, wherein the at least two attachment portions have the shape of a curved loop.

6. The intraocular implant according to claim 5, wherein a projection of each attachment portion on a plane containing the optical axis of the optical portion comprises a first portion close to the first end of the attachment portion, making a first angle with a plane orthogonal to the optical axis so that said first portion moves away from the front dioptric surface of the optical portion, and a second portion close to the second end of the attachment portion, making a second angle with the plane orthogonal to the optical axis so that said second portion moves closer to the front dioptric surface of the optical portion, whereby said optical portion substantially is not displaced in the direction of the optical axis under the effect of stresses applied to the implant.

7. The intraocular implant according to claim 3, wherein the outer edges of said lateral portions are substantially rectilinear, and the outer edges of the extensions have substantially the shape of a semi-circle, the outer edges of the lateral portions being connected to the outer edges of the extensions.

8. The intraocular implant according to claim 3, wherein the outer edges of the lateral portions are substantially rectilinear and projections of the attachment portions are in a plane orthogonal to the optical axis and are fully contained in a portion of said plane limited by two parallel lines, the parallel lines containing projections of the rectilinear outer edges of the lateral portions in the plane.

9. The intraocular implant according to claim 1, wherein the substantially circular optical portion has a diameter, the diameter being substantially in the range of 4 to 6 mm.

10. The intraocular implant according to claim 1, wherein the maximum distance between the outer edges of the extensions is substantially in the range of 7 to 9 mm.

11. The intraocular implant according to claim 4, wherein at least one hole is placed in at least one of the two extensions.

12. The intraocular implant according to claim 4, wherein at least one hole is placed in at least one of the two lateral portions.

13. The intraocular implant according to claim 3, wherein the attachment portions are in a plane orthogonal to the optical axis and do not extend beyond the outer edges of the lateral portions.

14. A posterior-chamber intraocular implant for correcting short-sightedness in a phakic eye having a natural lens, the implant comprising:

a substantially circular optical portion comprising a front dioptric surface and a rear dioptric surface and having a periphery, a diameter, and an optical axis;

at least two extensions, each extension having an inner edge connected to the periphery of the optical portion and an outer edge, a maximum distance between the outer edges of the extensions being greater than a diameter of a dilated pupil, each extension having a front surface and a rear surface, the front surface of each extension including a toroidal portion joined to the front dioptric surface, for allowing a posterior face of an iris of an eye to slide on the implant, the rear surface of each extension comprising a toroidal portion connected to the rear dioptric surface, the toroidal portion of the rear surface being structured to engage a periphery of a lens of an eye, and a connecting portion for connecting the toroidal portion with the outer edge of the extension, the connecting portions of the at least two extensions being disposed in a common surface, the rear dioptric surface and the toroidal positions of the rear surfaces of the extensions defining a recess with respect to the common surface for allowing a free altering of a curvature of a front surface of a lens of an eye; and two attachment portions distinct from the two extensions, each attachment portion having a first end connected to the outer edge of one of the two extensions and a second end being structured to be in contact with an inner wall of a posterior chamber of an eye, for attachment of the intraocular implant in an eye, each attachment portion having a shape of a curved loop.

15. The intraocular implant according to claim 14, wherein a projection of each attachment portion on a plane containing the optical axis of the optical portion comprises a first portion close to the first end of the attachment portion, making a first angle with a plane orthogonal to the optical axis so that the first portion moves away from the front dioptric surface of the optical portion, and a second portion close to the second end of the attachment portion, making a second angle with the plane orthogonal to the optical axis so that the second portion is closer to the front dioptric surface of the optical portion, whereby the optical portion is not substantially displaced in the direction of the optical axis under the effect of stresses applied to the implant.

16. The intraocular implant according to claim 14, wherein the outer edges of the lateral portions are substantially rectilinear, the outer edges of the lateral portions being connected to the outer edges of the extensions.

17. The intraocular implant according to claim 16, wherein projections of the attachment portions in a plane orthogonal to the optical axis are fully contained in a portion of the plane limited by two parallel lines, the parallel lines containing projections of the rectilinear outer edges of the lateral portions in the plane.

18. The intraocular implant according to claim 14, wherein the diameter of the substantially circular optical portion is substantially in the range of 4 to 6 millimeters.

19. The intraocular implant according to claim 14, wherein the maximum distance between the outer edges of the extensions is substantially in the range of 7 to 9 millimeters.

* * * * *